United States Patent
Lee et al.

(10) Patent No.: US 8,625,095 B2
(45) Date of Patent: Jan. 7, 2014

(54) AUTOMATIC INSPECTION APPARATUS FOR DETECTING STAINS ON POLARIZING PLATE USING COLOR DIFFERENCE ANALYSIS AND INSPECTION METHOD THEREOF

(75) Inventors: Chong-Kun Lee, Daejeon (KR); Kyun-Il Rah, Daejeon (KR); Tae-Hun Kim, Cheongju-si (KR); Yoo-Min Lee, Chuncheongbuk-do (KR); Sang-Deok Lee, Cheongju-si (KR)

(73) Assignee: LG Chem, Ltd., Seoul (KR)

( * ) Notice: Subject to any disclaimer, the term of this patent is extended or adjusted under 35 U.S.C. 154(b) by 32 days.

(21) Appl. No.: 13/457,078

(22) Filed: Apr. 26, 2012

(65) Prior Publication Data
US 2012/0274939 A1    Nov. 1, 2012

(30) Foreign Application Priority Data

Apr. 28, 2011 (KR) .................. 10-2011-0040370
Apr. 28, 2011 (KR) .................. 10-2011-0040371

(51) Int. Cl.
*G01J 4/00* (2006.01)
(52) U.S. Cl.
USPC .......................................... 356/364; 356/370
(58) Field of Classification Search
USPC .................................................. 356/364–370
See application file for complete search history.

(56) References Cited

U.S. PATENT DOCUMENTS

| 6,064,462 A | 5/2000 | Takeuchi et al. |
| 2009/0153849 A1* | 6/2009 | Moriya ................. 356/239.2 |

FOREIGN PATENT DOCUMENTS

| JP | 09229817 | 9/1997 |
| JP | 2001041716 | 2/2001 |
| JP | 2001116925 | 4/2001 |
| JP | 2005134573 | 5/2005 |
| JP | 2008008787 | 1/2008 |
| JP | 2010256564 | 11/2010 |
| JP | 2010534351 | 11/2010 |
| WO | 2009088212 | 7/2009 |

* cited by examiner

*Primary Examiner* — Tri T Ton
(74) *Attorney, Agent, or Firm* — McKenna, Long & Aldridge, LLP.

(57) ABSTRACT

There is provided an automatic inspection apparatus and method for detecting stains on a polarizing plate using color difference analysis. The automatic inspection apparatus includes an inspection unit including at least one reference polarizing plate and a target polarizing plate or polarizing element mounted on the at least one reference polarizing plate; a light source unit disposed on one surface of the inspection unit and irradiating the inspection unit with light; an imaging unit disposed on the other surface of the inspection unit, imaging the target polarizing plate or polarizing element, and transferring an image thereof; and an arithmetic operation unit performing color difference analysis for individual inspection regions of the image of the target polarizing plate or polarizing element transferred by the imaging unit and detecting a blurred stain.

23 Claims, 4 Drawing Sheets

AUTOMATIC INSPECTION APPARATUS FOR DETECTING STAINS ON POLARIZING PLATE USING COLOR DIFFERENCE ANALYSIS AND INSPECTION METHOD THEREOF

CROSS-REFERENCE TO RELATED APPLICATIONS

This application claims the priorities of Korean Patent Application Nos. 10-2011-0040370 filed on Apr. 28, 2011 and 10-2011-0040371 filed on Apr. 28, 2011, in the Korean Intellectual Property Office, the disclosures of which are incorporated herein by reference.

BACKGROUND OF THE INVENTION

1. Field of the Invention

The present invention relates to an automatic inspection apparatus and method for detecting stains on a polarizing plate, and more particularly, to an automatic inspection apparatus and method for detecting stains on a polarizing plate, designed to objectively determine the degree of staining on a polarizing plate using color difference analysis, monitor defects in a polarizing plate in a production line in real time, and automatically inspect the quality of a polarizing plate after cutting thereof.

2. Description of the Related Art

A polarizing plate is an optical device used to allow light polarized in a certain direction to be transmitted to a liquid crystal display (LCD) device. In general, the polarizing plate is manufactured by dyeing, cross-linking and elongating a polyvinyl alcohol (PVA) film.

According to the related art, a general polarizing plate manufacturing process includes dipping and dyeing a PVA film in a solution containing iodine or dye, cross-linking the iodine or dye with the PVA film by adding boric acid or the like thereto, and elongating the PVA film. The dyeing, cross-linking and elongating processes may be conducted consecutively or simultaneously, and the order of these individual processes may also be varied. After the PVA film is completely subjected to the dyeing, cross-linking and elongating processes, it may be dried to thereby form a PVA polarizer. A protective film such as a triacetyl cellulose (TAC) film is attached to one surface or both surfaces of the PVA polarizer using a PVA adhesive or the like, and thus, a polarizing plate is manufactured.

However, striped stains may be present on the polarizing plate manufactured as described above in a machine direction (MD) thereof due to uneven dyeing, poor attachment, or the like. When stains are severely formed thereon, the brightness of a screen is not uniform, and thus, final product defects may result therefrom. Therefore, a sorting operation is required to pick out defective products by measuring the degree of staining on polarizing plates. In general, the inspection of stains on the polarizing plates is carried out with the naked eye by human inspectors. However, this inspection method has problems in that it may be difficult to produce products having uniform product quality since the degree of defects in final products is subjectively determined by the inspectors.

Accordingly, in recent years, a method of quantifying the degree of staining on a polarizing plate has been sought. As a result, the following inspection apparatus and method have been provided: arranging a target polarizing plate to be disposed between reference polarizing plates having parallel absorption axes while an absorption axis of the target polarizing plate is perpendicular to those of the reference polarizing plates; quantifying the degree of staining on the target polarizing plate using intensity (contrast) data from among image data obtained by imaging the target polarizing plate while being irradiated with light; and objectively inspecting the stains on the target polarizing plate.

In such an inspection method, however, since the absorption axes of the reference polarizing plates and the target polarizing plate are perpendicular to each other, an amount of light transmitted through the target polarizing plate is so small that an exposure time of an imaging apparatus should be relatively lengthened in order to obtain analyzable image data. An excessive exposure time may cause a difference between stains obtained from RGB data extracted from the image data and stains observed with the naked eye by inspectors. Further, according to the related art, stains are quantified by utilizing intensity data from among the extracted image data, and accordingly, it is difficult to verify stains caused by a delicate color difference.

In order to solve the above-mentioned problems, developments in the quantification of stains on a polarizing plate and automatic inspection apparatus and inspection method are required.

SUMMARY OF THE INVENTION

An aspect of the present invention provides an automatic inspection apparatus and method for detecting stains on a polarizing plate using color difference analysis allowing for accurate inspection results of actual stains by image data analysis, without processing an image of a target polarizing plate into analyzable image data.

According to an aspect of the present invention, there is provided an automatic inspection apparatus for detecting stains on a polarizing plate using color difference analysis, the automatic inspection apparatus including: an inspection unit including at least one reference polarizing plate and a target polarizing plate or polarizing element mounted on the at least one reference polarizing plate; a light source unit disposed on one surface of the inspection unit and irradiating the inspection unit with light; an imaging unit disposed on the other surface of the inspection unit, imaging the target polarizing plate or polarizing element, and transferring an image thereof; and an arithmetic operation unit performing color difference analysis for individual inspection regions of the image of the target polarizing plate or polarizing element transferred by the imaging unit and detecting a blurred stain.

According to another aspect of the present invention, there is provided an automatic inspection method of detecting stains on a polarizing plate using color difference analysis, the automatic inspection method including: mounting a target polarizing plate or polarizing element on at least one reference polarizing plate; irradiating the target polarizing plate or polarizing element with light; imaging the target polarizing plate or polarizing element; and calculating color differences between individual pixels using data extracted from an image captured through the imaging of the target polarizing plate or polarizing element.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE EMBODIMENTS

Figure 1:
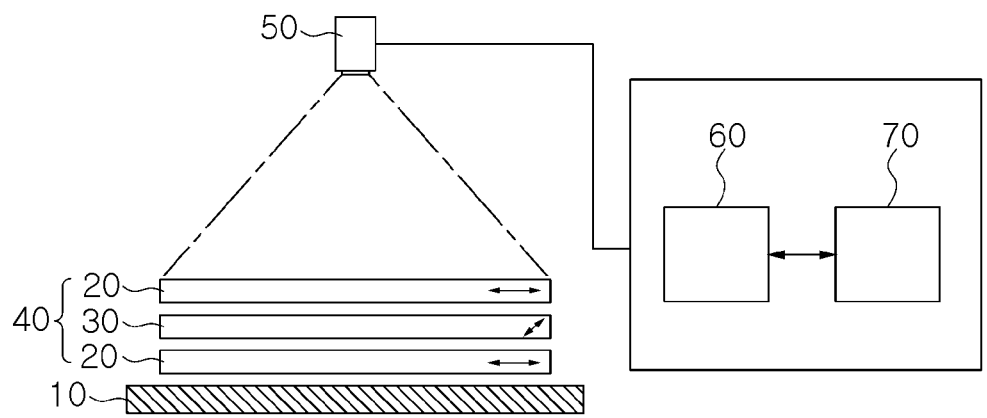
FIG. 1 shows the configuration of an automatic inspection apparatus for detecting stains on a polarizing plate using color difference analysis according to an embodiment of the present invention.

Embodiments of the present invention will now be described in detail with reference to the accompanying drawings.

The invention may, however, be embodied in many different forms and should not be construed as bing limited to the embodiments set forth herein. Rather, these embodiments are provided so that this disclosure will be thorough and complete, and will fully convey the scope of the invention to those skilled in the art.

In the drawings, the shapes and dimensions of components may be exaggerated for clarity.

Figure 2:
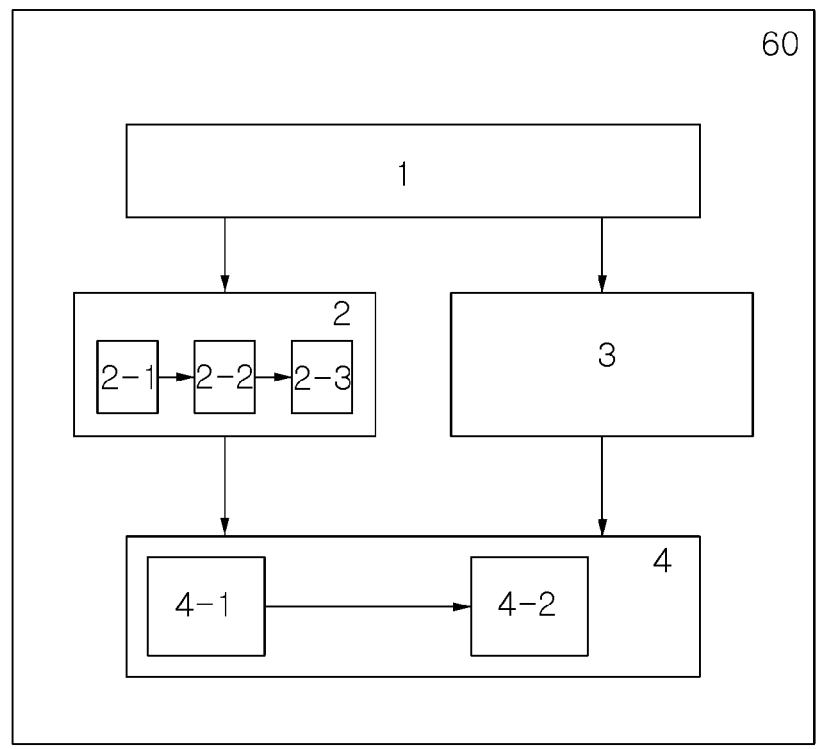
FIG. 2 shows the configuration of an arithmetic operation unit in an automatic inspection apparatus for detecting stains on a polarizing plate using color difference analysis according to an embodiment of the present invention.
Figure 3:
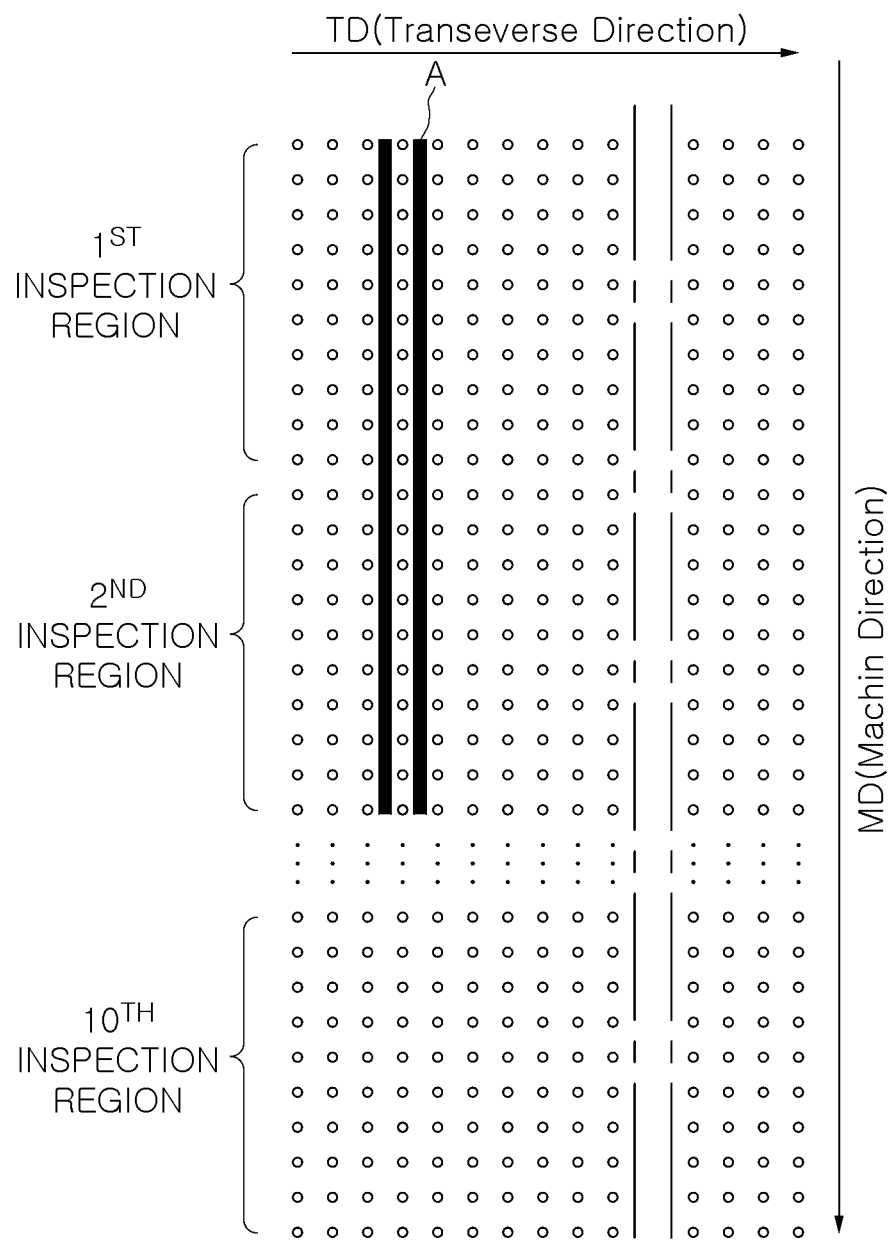
FIG. 3 shows an example of inspection regions set by an inspection region setting unit in an automatic inspection apparatus for detecting stains on a polarizing plate using color difference analysis according to an embodiment of the present invention.
Figure 4:
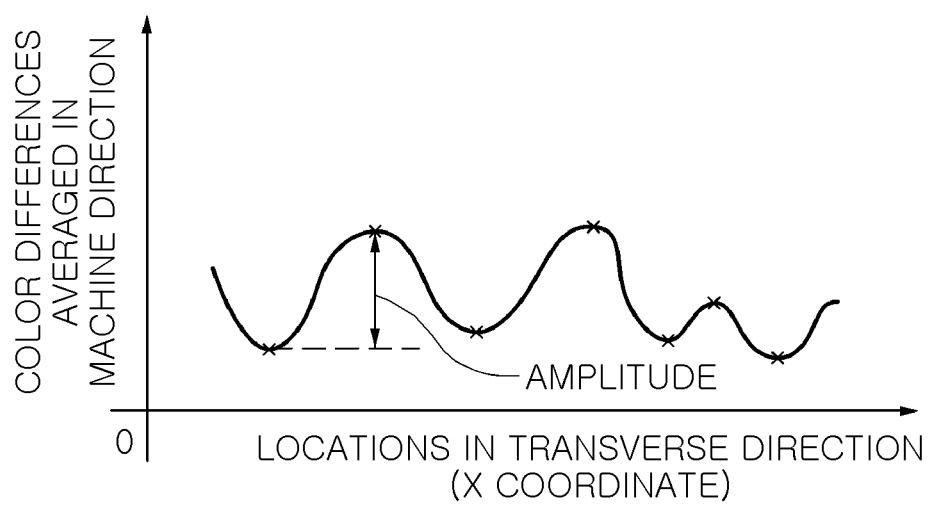
FIG. 4 is a graph showing color differences in a transverse direction (TD) obtained by an automatic inspection apparatus for detecting stains on a polarizing plate using color difference analysis according to an embodiment of the present invention.
Figure 5:
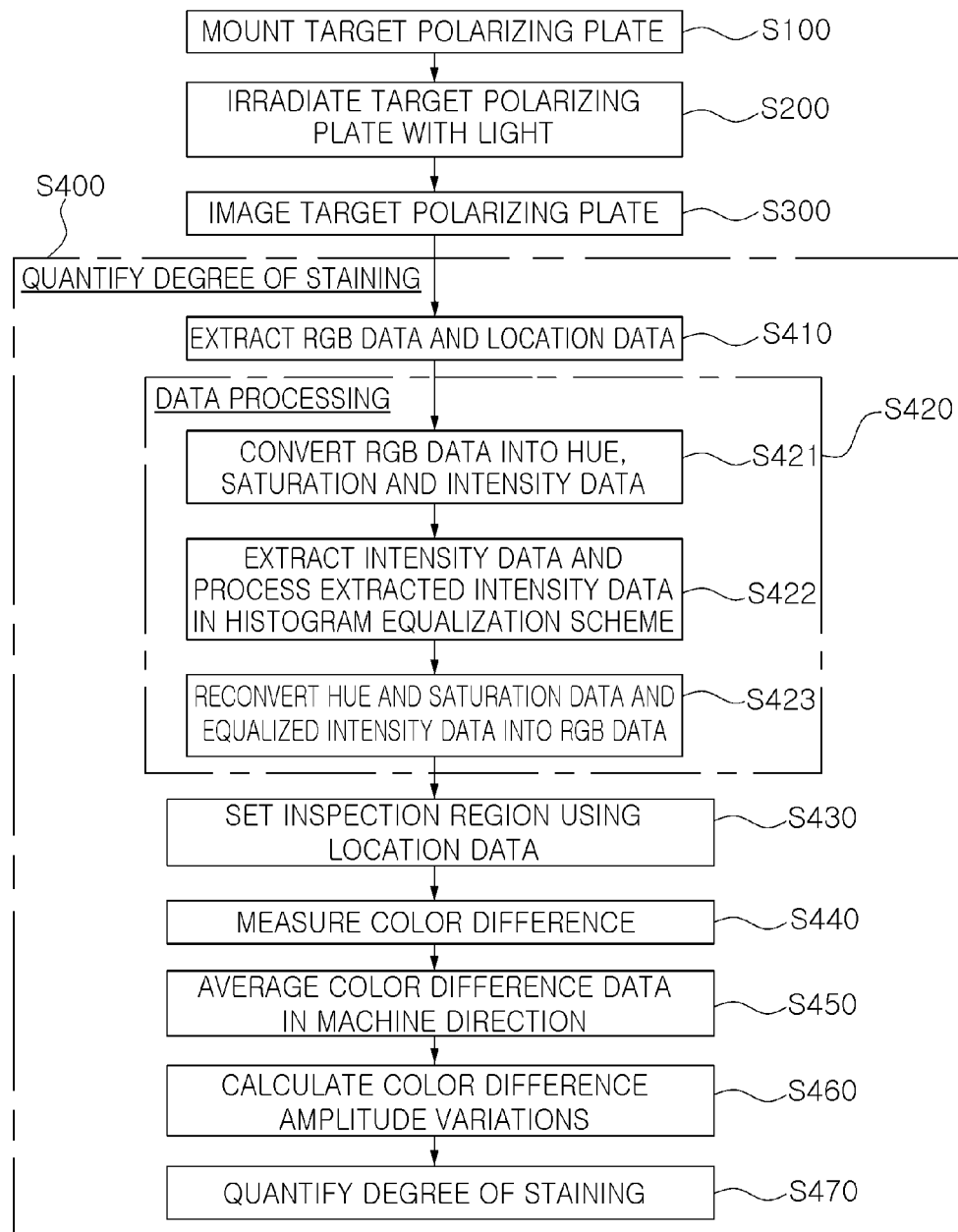
FIG. 5 is a flowchart illustrating an automatic inspection method of detecting stains on a polarizing plate using color difference analysis according to an embodiment of the present invention.

FIG. 1 shows the configuration of an automatic inspection apparatus for detecting stains on a polarizing plate using color difference analysis according to an embodiment of the present invention; FIG. 2 shows the configuration of an arithmetic operation unit in an automatic inspection apparatus for detecting stains on a polarizing plate using color difference analysis according to an embodiment of the present invention; and FIG. 3 shows an example of inspection regions set by an inspection region setting unit in an automatic inspection apparatus for detecting stains on a polarizing plate using color difference analysis according to an embodiment of the present invention. FIG. 4 is a graph showing color differences in a transverse direction (TD) obtained by an automatic inspection apparatus for detecting stains on a polarizing plate using color difference analysis according to an embodiment of the present invention; and FIG. 5 is a flowchart illustrating an automatic inspection method of detecting stains on a polarizing plate using color difference analysis according to an embodiment of the present invention.

With reference to FIGS. 1 through 3, an automatic inspection apparatus for detecting stains on a polarizing plate using color difference analysis according to an embodiment of the present invention includes a light source unit 10, an inspection unit 90, an imaging unit 50, and an arithmetic operation unit 60, and may further include a display unit 70 as necessary.

Hereinafter, individual units in an automatic inspection apparatus for detecting stains on a polarizing plate according to an embodiment of the present invention will be described in detail.

(1) Light Source Unit

The light source unit 10 functions to render stains visible by irradiating the inspection unit 40 with light. As shown in FIG. 1, the light source unit 10 may be disposed on one surface (for example, a lower surface) of the inspection unit 40. Further, a backlight, a light emitting diode (LED) light source, or the like, generally used in a display device, may be used therefor.

Here, the intensity of the light source unit 10 may be set to allow a level of brightness of the inspection unit 40 to be 2.5 to 20 nits. Here, 'nit' refers to a unit of surface brightness equal to 1 cd/m2 or 0.00001sb.

(2) Inspection Unit

The inspection unit 40 includes at least one reference polarizing plate 20 and a target polarizing plate or polarizing element to be inspected 30. The target polarizing plate or polarizing element 30 may be mounted on at least one reference polarizing plate 20.

A polarizing plate, a half-finished polarizing plate, a polarizing element, or the like, generally used in the art to which the present invention pertains, may be used as the reference polarizing plate 20. For example, the reference polarizing plate 20 may be a half-finished polarizing plate using a clear triacetyl cellulose (TAC) film on which surface coating has not been undertaken, such as 'UZ-TAC' manufactured by Fujifilm Corporation, having a level of transmittance of 41.0% to 42.5%.

Further, at least one reference polarizing plate may be used, but at least two reference polarizing plates may be preferably used. This is because polarized light may be varied due to several factors and a single polarizing plate may fail to completely absorb polarizing components in parallel to an absorption axis thereof.

In a case in which at least two reference polarizing plates 20 are used, their absorption axes may be parallel to each other. At least two reference polarizing plates having the parallel absorption axes may maximize absorption of polarizing components in parallel to the absorption axes thereof and minimize components other than polarizing components in parallel to a transmission axis of the target polarizing plate or polarizing element, whereby stain visibility may be improved.

Meanwhile, the polarizing plate or polarizing element 30 manufactured in a production line may be transferred to the inspection unit 40 and mounted on at least one reference polarizing plate, or more preferably, may be disposed between at least two reference polarizing plates. This is intended to improve stain visibility by maximizing an absorption rate of polarizing components in parallel to the absorption axes of the reference polarizing plates. In general, polarized light may be varied due to several factors and polarizing components in parallel to an absorption axis of a polarizing plate may transmit the polarizing plate. Accordingly, a single polarizing plate may fail to completely absorb polarizing components in parallel to an absorption axis thereof. For this reason, the target polarizing plate or polarizing element is disposed between at least two reference polarizing plates to thereby maximize absorption of polarizing components in parallel to the absorption axes of the reference polarizing plates and minimize components other than polarizing components in parallel to a transmission axis of the target polarizing plate or polarizing element, whereby stain visibility may be improved.

In the mounting of the target polarizing plate or polarizing element 30, the absorption axis of the target polarizing plate or polarizing element 30 may be inclined with respect to the absorption axes of the reference polarizing plates in order to allow a level of brightness of the inspection unit 40 to be 2.5 to 20 nits, more preferably 2.5 to 15 nits, and most preferably 5 to 10 nits, while being irradiated with light. This may facilitate obtaining an image allowing for stain analysis. In a case in which the level of brightness of the inspection unit 40 having the target polarizing plate or polarizing element 30 is less than 2.5 nits, an amount of light passing through the target polarizing plate or polarizing element 30 is excessively small such that a considerable amount of time is required to obtain an image allowing for stain analysis. In a case in which the level of brightness of the inspection unit 40 having the target polarizing plate or polarizing element 30 exceeds 20 nits, an amount of light passing through the target polarizing plate or polarizing element 30 is too great to precisely image stains on the target polarizing plate or polarizing element 30. Thus, it is difficult to precisely detect stains on the polarizing plate. Further, in a case in which the absorption axes of the reference polarizing plates 20 and the target polarizing plate or polarizing element 30 are perpendicular to each other, even when the target polarizing plate or polarizing element 30 is irradiated with light by the light source unit, an amount of light passing through the target polarizing plate or polarizing element 30 is excessively small such that a considerable amount of time is required to obtain an image allowing for stain analysis. Therefore, the absorption axes of the reference polarizing plates 20 and the target polarizing plate or polarizing element 30 may be inclined with regard to each other so as to secure a certain amount of light. In addition, target polarizing plates or polarizing elements have different levels of transmittance, such that the absorption axes of the reference polarizing plates and the target polarizing plates or polarizing elements do not need to be within a certain range of angles, but may be arranged to have a certain level of brightness.

Meanwhile, the inspection unit 90 may further include a rotating unit (not shown) for rotating the target polarizing plate or polarizing element 30, such that the target polarizing plate or polarizing element 30 may be rotated to allow the inspection unit 40 to have a desired level of brightness. In the case in which the rotating unit is included, the inspection unit 40 may further include a measuring unit (not shown) for measuring a level of brightness of the inspection unit 40 and a controlling unit (not shown) for controlling the rotating unit according to a brightness value transferred by the measuring unit to determine an angle of rotation of the target polarizing plate or polarizing element 30. This may facilitate control of the angle of rotation of the target polarizing plate or polarizing element 30 to allow the inspection unit 40 to have a desired level of brightness.

Meanwhile, the inspection unit 40 may further include a second rotating unit (not shown) for rotating a reference polarizing plate, disposed in a direction toward the imaging unit, of at least two reference polarizing plates, as well as a first rotating unit (not shown) for rotating the target polarizing plate or polarizing element. In this case, the inspection unit 40 may further include a measuring unit (not shown) for measuring a level of brightness of the inspection unit 40 and a controlling unit (not shown) for controlling the first rotating unit according to a brightness value transferred by the measuring unit to determine an angle of rotation of the target polarizing plate or polarizing element and controlling the second rotating unit based on an image captured by the imaging unit to determine an angle of rotation of the reference polarizing plate disposed in the direction toward the imaging unit. These additional units are provided to control the angle of rotation of the target polarizing plate or polarizing element to allow the inspection unit 40 to have a desired level of brightness and control the angle of rotation of the reference polarizing plate disposed in the direction toward the imaging unit by verifying stain visibility on the captured image.

(3) Imaging Unit

The imaging unit 50 is provided to capture an image of the target polarizing plate or polarizing element 30 on which stains are rendered visible through light irradiated by the light source unit 10. As shown in FIG. 1, the imaging unit 50 may be disposed above the other surface of the inspection unit 40 on an opposite side thereof to the light source unit 10 (for example, an upper part of the inspection unit 40). In the embodiment of the present invention, a general digital camera, a CCD camera, a high speed camera or the like may be used therefor. The captured image of the target polarizing plate or polarizing element 30 may be transferred to the arithmetic operation unit 60. In general, the image includes RGB data, location data, and other data of individual pixels.

(4) Arithmetic Operation Unit

The arithmetic operation unit 60 performs color difference analysis through a series of operations with regard to individual inspection regions from the image transferred by the imaging unit 50 and quantifies the degree of staining on the target polarizing plate or polarizing element 30 as a numerical data value using the analyzed results. To enable this, the arithmetic operation unit 60 includes a data extracting unit 1, a data processing unit 2, an inspection region setting unit 3, and a color difference analyzing unit 4.

The data extracting unit 1 extracts location data and RGB data from the image transferred by the imaging unit 50 in order to set location regions and calculate color differences for the detection and quantification of stains.

The data processing unit 2 processes the RGB data extracted by the data extracting unit 1 to allow a contrast range to be high. This is intended to allow stains difficult to be observed with the naked eye to be rendered visible by increasing a contrast range as compared to that of an actually captured image.

Specifically, the data processing unit 2 includes a converting part 2-1, a processing part 2-2, and a reconverting part 2-3.

Here, the converting part 2-1 converts the RGB data extracted by the data extracting unit 1 into hue, saturation and intensity data (commonly referred to as 'HSI data'). This is because HSI data may be easily processed as compared to RGB data.

The processing part 2-2 extracts intensity data from the HSI data converted by the converting part 2-1 and processes the extracted intensity data in a histogram equalization scheme. Here, 'histogram equalization' refers to a method of contrast adjustment using the image's histogram in image processing, thereby allowing an image having low contrast distribution to be uniformly equalized. The intensities of the image may be redistributed to thereby maximize contrast values. The histogram equalization process is performed in a conventional way.

The reconverting part 2-3 combines the intensity data processed in the histogram equalization scheme in the processing part 2-2 with the hue and saturation data and reconverts the combined data into RGB data. This is intended to calculate color differences between individual pixels by reconverting the HSI data into the RGB data.

The inspection region setting unit 3 sets inspection regions using location data of individual pixels extracted by the data extracting unit 1. The inspection regions are appropriately divided to thereby improve accuracy in the quantification of stains and efficiency in terms of inspection speed.

The inspection regions set by the inspection region setting unit 3 are described with reference to FIG. 3.

Each inspection region may contain a plurality of pixels equal to or less than $\frac{1}{10}$ of a total number of pixels in a machine direction (MD) of the captured image of the target polarizing plate or polarizing element 30. This is intended to allow for detection of a blurred stain A and quantify the degree of staining thereof. In a case in which the number of pixels contained in each inspection region exceeds ⅒ of the total number of pixels in the machine direction (MD) of the captured image of the target polarizing plate or polarizing element 30, it may be difficult to obtain a valid value with regard to the blurred stain A.

The inspection region may contain at least 10 pixels, more preferably 100 pixels or more, in the machine direction (MD) of the captured image of the target polarizing plate or polarizing element 30. This is intended to secure efficiency in the quantification of a blurred stain.

The color difference analyzing unit 4 performs detection and quantification of blurred stains by analyzing color differences in the RGB data processed by the data processing unit 2 with regard to the inspection regions set by the inspection region setting unit 3.

With reference to FIGS. 2 and 3, the color difference analyzing unit 4 includes a color difference calculating part 4-1 and a detecting part 4-2.

The color difference calculating part 4-1 calculates color differences of individual pixels within each of the inspection regions ($1^{st}$ to $10^{th}$ inspection regions) set by the inspection region setting unit 3.

Here, the color difference calculation process is as follows:

Color coordinates (for example, CIELAB's color coordinates (L*,a*,b*)) of all pixels within all the inspection regions of the captured image of the target polarizing plate or polarizing element 30 are identified to set the most probable value as a reference value (color coordinates ($L_1^*, a_1^*, b_1^*$) of the reference value).

Color differences in all individual pixels (color coordinates ($L_2^*, a_2^*, b_2^*$) of each pixel) within the inspection regions are calculated by the following Equation 1:

$$\Delta E_{ab}^* = \sqrt{(L_2^* - L_1^*)^2 + (a_2^* - a_1^*)^2 + (b_2^* - b_1^*)^2} \quad \text{Equation 1}$$

Here, ($L_1^*, a_1^*, b_1^*$) denote the color coordinates of the reference value, ($L_2^*, a_2^*, b_2^*$) denote the color coordinates of each pixel, and $\Delta E_{ab}^*$ denotes a color difference in each pixel.

An average color difference value is calculated in the machine direction (MD) of the captured image. With reference to FIG. 3, this means that an average color difference value is calculated for each column in the machine direction (MD).

The detecting part 4-2 detects the blurred stain A by analyzing the color differences calculated by the color difference calculating part 4-1 and quantifies, the degree of staining. A detailed process thereof is as follows:

The average color difference values calculated in the machine direction (MD) by the color difference calculating part 4-1 are represented as a graph based on location values in a transverse direction (TD). FIG. 4 is a graph showing the relationship between the average color difference values in the machine direction (MD) and the location values in the transverse direction (TD).

The average color difference values are checked in the transverse direction (TD) to determine local maximum and minimum values in each column. When the local maximum and minimum values are greater than a predetermined critical value, they are stored and used to calculate a maximum color difference amplitude value. Here, the predetermined critical value may be appropriately set, and is generally set as a maximum amplitude value that may be determined as noise.

The calculated maximum color difference amplitude value is compared with predetermined numerical data values indicating the degree of staining, such that the degree of staining on the target polarizing plate or polarizing element may be quantified. As an example of the predetermined numerical data values indicating the degree of staining, when a color difference amplitude value is 0 to 4, a numerical data value is 5; when a color difference amplitude value is 5 to 8, a numerical data value is 4; when a color difference amplitude value is 9 to 12, a numerical data value is 3; when a color difference amplitude value is 13 to 16, a numerical data value is 2; and when a color difference amplitude value is 17 to 20, a numerical data value is 1. Here, the numerical data value '5' means that stains are not detected when being observed with the naked eye, while the numerical data value '1' means that stains are clearly visible when being observed with the naked eye.

The above-described operations in the color difference analyzing unit 4 may be conducted using a conventional program commonly used in the art to which the present invention pertains. The operations may be conducted with regard to the inspection regions simultaneously or individual inspection regions sequentially.

(5) Display Unit

The automatic inspection apparatus may further include the display unit 70. Specifically, the display unit 70 may display the calculation results of the arithmetic operation unit 60 and/or the degree of staining using a gray scale image. In this case, inspectors may verify the degree of staining on the target polarizing plate or polarizing element in real time.

Meanwhile, the automatic inspection apparatus for detecting stains on a polarizing plate using color difference analysis according to the embodiment of the invention is directly installed in a production line, such that stains on a polarizing plate may be inspected in the production line in real time.

The automatic inspection apparatus for detecting stains on a polarizing plate using color difference analysis according to the embodiment of the invention may monitor the degree of staining on polarizing plates in the production line in real time, without inspectors' inspection of individual polarizing plates. Accordingly, quality control and production efficiency are enhanced, and production time is reduced. In the automatic inspection apparatus, a target polarizing plate is arranged to have a certain level of brightness when an image thereof is captured, an image suitable for stain analysis may be easily obtained. Further, data extracted from the captured image is processed to increase a contrast range, and accordingly, a blurred stain may be detected more precisely. In addition, the automatic inspection apparatus quantifies the degree of staining on polarizing plates based on an objective standard, whereby product quality may be uniformly maintained.

Hereinafter, a method of detecting stains on a polarizing plate using color difference analysis according to an embodiment of the present invention will be described in detail.

With reference to FIG. 5, an automatic inspection method of detecting stains on a polarizing plate using color difference analysis includes mounting a target polarizing plate in operation S100, irradiating the target polarizing plate with light in operation S200, imaging the target polarizing plate in operation S300, and quantifying the degree of staining on the target polarizing plate in operation S400.

In the mounting operation S100 of the target polarizing plate, the target polarizing plate or polarizing element 30 is mounted on at least one reference polarizing plate 20.

Here, a polarizing plate, a half-finished polarizing plate, a polarizing element, or the like, generally used in the art to which the present invention pertains, may be used as the reference polarizing plate 20. For example, the reference polarizing plate 20 may be a half-finished polarizing plate using a clear triacetyl cellulose (TAC) film on which surface coating has not been undertaken, such as 'UZ-TAC' manufactured by Fujifilm Corporation, having a level of transmittance of 41.0% to 42.5%.

Further, at least one reference polarizing plate 20 may be used, but at least two reference polarizing plates may preferably be used. This is because polarized light may be varied due to several factors and a single polarizing plate may fail to completely absorb polarizing components in parallel to an absorption axis thereof.

In a case in which at least two reference polarizing plates 20 are used, their absorption axes may be parallel to each other. At least two reference polarizing plates having the parallel absorption axes may maximize absorption of polarizing components in parallel to the absorption axes thereof and minimize components other than polarizing components in parallel to a transmission axis of the target polarizing plate or polarizing element, whereby stain visibility may be improved.

Meanwhile, in the mounting operation S100 of the target polarizing plate, the target polarizing plate or polarizing element 30 may be mounted on at least one reference polarizing plate 20, or more preferably, may be disposed between at least two reference polarizing plates 20. This is intended to improve stain visibility by maximizing an absorption rate of polarizing components in parallel to the absorption axes of the reference polarizing plates. In general, polarized light may be varied due to several factors and polarizing components in parallel to an absorption axis of a polarizing plate may transmit the polarizing plate. Accordingly, a single polarizing plate may fail to completely absorb polarizing components in parallel to an absorption axis thereof. For this reason, the target polarizing plate or polarizing element is disposed between at least two reference polarizing plates to thereby maximize absorption of polarizing components in parallel to the absorption axes of the reference polarizing plates and minimize components other than polarizing components in parallel to a transmission axis of the target polarizing plate or polarizing element, whereby stain visibility may be improved.

In the mounting operation S100, the target polarizing plate or polarizing element 30 may be arranged such that the absorption axis of the target polarizing plate or polarizing element 30 is inclined with respect to the absorption axes of the reference polarizing plates in order to allow a level of brightness to be 2.5 to 20 nits, more preferably 2.5 to 15 nits, and most preferably 5 to 10 nits while being irradiated with light. Alternatively, the target polarizing plate or polarizing element may be rotated between the irradiating operation S200 and the imaging operation S300 such that the absorption axis of the target polarizing plate or polarizing element 30 is inclined with respect to the absorption axes of the reference polarizing plates 20 in order to allow a level of brightness to be 2.5 to 20 nits, more preferably 2.5 to 15 nits, and most preferably 5 to 10 nits.

Here, 'nit' refers to a unit of surface brightness equal to 1 cd/m2 or 0.00001sb. The inclined arrangement of the absorption axes of the target polarizing plate or polarizing element and the reference polarizing plates so as to have a certain range of brightness is intended to easily obtain an image allowing for stain analysis. Specifically, in a case in which the level of brightness of the target polarizing plate or polarizing element 30 is less than 2.5 nits, an amount of light passing through the target polarizing plate or polarizing element 30 is excessively small such that a considerable amount of time is required to obtain an image allowing for stain analysis. In a case in which the level of brightness of the target polarizing plate or polarizing element 30 exceeds 20 nits, an amount of light passing through the target polarizing plate or polarizing element 30 is too great to precisely image stains on the target polarizing plate or polarizing element 30. Thus, it is difficult to precisely detect stains on the polarizing plate. Further, in a case in which the absorption axes of the reference polarizing plates 20 and the target polarizing plate or polarizing element 30 are perpendicular to each other, even when the target polarizing plate or polarizing element 30 is irradiated with light by the light source unit, an amount of light passing through the target polarizing plate or polarizing element 30 is excessively small such that a considerable amount of time is required to obtain an image allowing for stain analysis. Therefore, the absorption axes of the reference polarizing plates 20 and the target polarizing plate or polarizing element 30 may be inclined with regard to each other so as to secure a certain amount of light.

Next, in the irradiating operation S200, the target polarizing plate or polarizing element 30 may be irradiated with light by the light source unit 10. At this time, a backlight, a light emitting diode (LED) light source, or the like, generally used in a display device, may be used as the light source unit 10. The light source unit 10 may be disposed below the target polarizing plate or polarizing element 30 or in the rear thereof. Further, the intensity of the light source unit 10 may be set to allow a level of brightness of the target polarizing plate or polarizing element 30 to be 2.5 to 20 nits.

Thereafter, in the imaging operation S300, an image of the target polarizing plate or polarizing element 30 may be captured by the imaging unit 50. At this time, the imaging unit 50 may be disposed above the target polarizing plate or polarizing element 30 or in the front thereof. A general digital camera, a CCD camera, a high speed camera or the like may be used as the imaging unit 50.

Then, in the stain quantifying operation S400, data may be extracted from the captured image obtained in the imaging operation S300 and color differences may be calculated using the extracted data, and then the degree of staining may be quantified using the calculated color difference data. This process is performed by the arithmetic operation unit 60 such as a computer or the like.

The stain quantifying operation S400 is undertaken according to the following process:

First of all, data of individual pixels of the image captured in the imaging operation S300 may be extracted in operation S410. Here, the data of individual pixels includes location data and RGB data.

Next, the data of individual pixels extracted in operation S410 may be processed, if necessary, to increase a contrast range of the RGB data in operation S420.

The data processing operation S420 includes a data converting process S421, a data processing process 5422, and a data reconverting process S423.

In the data converting process 5421, the RGB data among the data of individual pixels extracted in operation S410 may be converted into hue, saturation and intensity data (HSI data). This is because HSI data may be easily processed as compared to RGB data.

In the data processing process S422, the intensity data may be extracted from the converted data in the data converting process S421 and may be subjected to histogram equalization. Here, 'histogram equalization' refers to a method of contrast adjustment using the image's histogram in image processing, thereby allowing an image having low contrast distribution to be uniformly equalized. The intensities of the image may be redistributed to thereby maximize contrast values. The histogram equalization process is performed in a conventional way.

In the data reconverting process S423, the intensity data processed in the histogram equalization scheme in the data processing process 5422 may be combined with the hue and saturation data, and the combined data may then be reconverted into RGB data.

Thereafter, locations of individual pixels from the data extracted in operation S410 are detected to set inspection regions in operation S430. That is, the inspection regions are set by using the location data of individual pixels.

Here, each inspection region may contain a plurality of pixels equal to or less than 1/10 of a total number of pixels in the machine direction (MD) of the captured image as shown in FIG. 3. This is intended to allow for detection of the blurred stain A and quantify the degree of staining thereof. In a case in which the number of pixels contained in each inspection region exceeds 1/10 of the total number of pixels in the machine direction (MD) of the captured image of the target polarizing plate or polarizing element, it may be difficult to obtain a valid value with regard to the blurred stain A.

The inspection region may contain at least 10 pixels, more preferably 100 pixels or more, in the machine direction (MD) of the captured image. This is intended to secure efficiency in quantification of a blurred stain.

Then, color differences between individual pixels may be measured in operation S440 by detecting color coordinates of individual pixels from the data extracted in operation S410 within the inspection region set in operation S430. That is, color coordinates may be detected from the RGB data of individual pixels within the inspection region and color differences between individual pixels may be calculated.

Specifically, the color difference calculation process is as follows: color coordinates (for example, CIELAB's color coordinates ($L^*$, $a^*$, $b^*$)) of all pixels within all the inspection regions of the captured image may be identified to set the most probable value as a reference value (color coordinates ($L_1^*$, $b_1^*$) of the reference value). Color differences in all individual pixels (color coordinates ($L_2^*$, $a_2^*$, $b_2^*$) of each pixel) within the inspection regions may be operated according to the following Equation 1:

$$\Delta E_{ab}^* = \sqrt{(L_2^*-L_1^*)^2 + (a_2^*-a_1)^2 + (b_2^*-b_1^*)^2}$$  Equation 1

Here, ($L_1^*$, $b_1^*$) denote the color coordinates of the reference value, ($L_2^*$, $a_2^*$, $b_2^*$) denote the color coordinates of each pixel, and $\Delta E_{ab}^*$ denotes a color difference in each pixel.

Then, the color difference data of individual pixels obtained in operation S440 may be averaged in the machine direction (MD) in operation S450. This means that an average color difference value is calculated for each column of the inspection region.

Then, the average color difference value obtained in operation S450 may be analyzed in the transverse direction (TD) to thereby calculate a maximum color difference amplitude value in operation S460. The average color difference values may be checked in the transverse direction (TD) to determine local maximum and minimum values in each column. When a local color difference amplitude value is greater than a predetermined critical value, it may be stored and used to calculate a maximum color difference amplitude value. Here, the predetermined critical value may be appropriately set, and is generally set as a maximum amplitude value that may be determined as noise.

Then, the maximum color difference amplitude value calculated in operation S460 may be compared with a predetermined numerical data value indicating the degree of staining, such that the degree of staining on the target polarizing plate or polarizing element may be quantified in operation S470. As an example of the predetermined numerical data values indicating the degree of staining, when a color difference amplitude value is 0 to 4, a numerical data value is 5; when a color difference amplitude value is 5 to 8, a numerical data value is 4; when a color difference amplitude value is 9 to 12, a numerical data value is 3; when a color difference amplitude value is 13 to 16, a numerical data value is 2; and when a color difference amplitude value is 17 to 20, a numerical data value is 1. Here, a numerical data value of '5' means that stains are not detected when observed with the naked eye, while a numerical data value of '1' means that stains are clearly visible when observed with the naked eye.

Meanwhile, the automatic inspection method for detecting stains on a polarizing plate using color difference analysis according to the embodiment of the invention may allow the numerical data value quantified in operation S470 to be displayed using the display unit such as a monitor or the like.

In the automatic inspection method for detecting stains on a polarizing plate using color difference analysis according to the embodiment of the invention, the target polarizing plate is arranged to have a certain level of brightness when an image thereof is captured, an image suitable for stain analysis may be easily obtained. Further, data extracted from the captured image is processed to increase a contrast range, and accordingly, a blurred stain may be detected more precisely. In addition, the degree of staining on polarizing plates may be quantified based on an objective standard, whereby product quality may be uniformly maintained.

Hereinafter, exemplary embodiments of the present invention will be described in detail.

Example 1

A non-elongated PVA film was dyed in a dye bath at a temperature of 25° C. to 30° C. for a retention time of 1 to 5 minutes, and elongated 5 to 6 times to thereby prepare a polarizing element. Here, 'UZ grade' having a haze and a thickness of 800n were used as a protective film of the polarizing element.

After the manufactured polarizing plate was mounted on a reference polarizing plate (manufactured by LG Chemicals, RB60SR10, a level of transmittance: 39.7%), it was irradiated with light using a 42-inch backlight (LG display, a color temperature of 10,000K). Here, an absorption axis of the manufactured polarizing plate was inclined with respect to that of the reference polarizing plate in order to allow a level of brightness of the manufactured polarizing plate to be 5 nits, while being irradiated with light. Thereafter, an image of the polarizing plate was captured above the backlight using a digital camera (Nikon, D3100 Zoom lens), and the captured image was transferred to a computer. The computer extracted data of individual pixels from the image, converted RGB data among the extracted data into hue, saturation and intensity data (HSI data), processed the intensity data extracted from the converted HIS data in a histogram equalization scheme, combined the equalized intensity data with the hue and saturation data, and reconverted the HSI data into RGB data. The computer program was designed to divide the whole image of 4608×3000 pixels into 10 inspection regions, calculate color differences in all 4608×300 pixels within individual inspection regions, average color difference values of 300 pixels in a machine direction (MD), analyze 4608 average color difference values in a transverse direction (TD), calculate and save maximum amplitude values in the inspection regions, and display the saved maximum amplitude values. Here, the program utilized Image J and C++ sources. Also, the saved maximum amplitude values were compared with predetermined numerical data values indicating the degree of staining, thereby quantifying the degree of staining. The predetermined numerical data values were set as follows: when a color difference amplitude value was 0 to 4, a numerical data value was set as 5; when a color difference amplitude value was 5 to 8, a numerical data value was set as 4; when a color difference amplitude value was 9 to 12, a numerical data value was set as 3; when a color difference amplitude value was 13 to 16, a numerical data value was set as 2; and when a color difference amplitude value was greater than 17, a numerical data value was set as 1. Here, a numerical data value of '5' represented that stains were not detected when observed with the naked eye, while a numerical data value of '1' represented that stains were clearly visible when observed with the naked eye. As a result of inspection of the polarizing plate, the maximum amplitude value and the numerical data value indicating the degree of staining thereof were stated in Table 1.

Example 2

A polarizing plate was prepared in the same manner as in Example 1, except that 'WVEA' (manufactured by Fujifilm Corporation, having a thickness of 60 μm) and 'UZ Clear TAC' (manufactured by Fujifilm Corporation, having a thickness of 60 μm) were used as a protective film. The manufactured polarizing plate was subjected to the same process as in Example 1 to calculate a maximum amplitude value and quantify the degree of staining. As a result of inspection of the polarizing plate, the maximum amplitude value and the numerical data value indicating the degree of staining thereof were stated in Table 1.

Example 3

A polarizing plate was prepared in the same manner as in Example 1, except that 'UZ' and 'UZ Clear' having a thickness of 60 μm were used as a protective film. The manufactured polarizing plate was subjected to the same process as in Example 1 to calculate a maximum amplitude value and quantify the degree of staining. As a result of inspection of the polarizing plate, the maximum amplitude value and the numerical data value indicating the degree of staining thereof were stated in Table 1.

Example 4

A polarizing plate was prepared in the same manner as in Example 1, except that 'Hard Coating Grade' (manufactured by Konica Corporation, having a thickness of 40 μm) and 'UZ Clear' (manufactured by Konica Corporation, having a thickness of 40 μm) were used as a protective film. The manufactured polarizing plate was subjected to the same process as in Example 1 to calculate a maximum amplitude value and quantify the degree of staining. As a result of inspection of the polarizing plate, the maximum amplitude value and the numerical data value indicating the degree of staining thereof were stated in Table 1.

Example 5

A non-elongated PVA film was dyed in a dye bath at a temperature of 25° C. to 30° C. for a retention time of 1 to 5 minutes, and elongated 5 to 6 times to thereby prepare a polarizing element. Here, 'WVEA' and 'UZ Haze' having a thickness of 60 μm were used as a protective film of the polarizing element. The manufactured polarizing plate was subjected to the same process as in Example 1 to calculate a maximum amplitude value and quantify the degree of staining. As a result of inspection of the polarizing plate, the maximum amplitude value and the numerical data value indicating the degree of staining thereof were stated in Table 1.

TABLE 1

| | Maximum Color Difference Amplitude Value | Numerical Data Value Indicating Degree of Staining |
|---|---|---|
| Example 1 | 9.28 | 3 |
| Example 2 | 6.32 | 4 |
| Example 3 | 3.82 | 5 |
| Example 4 | 23.63 | 1 |
| Example 5 | 12.78 | 2 |

As shown in Table 1, the degree of staining was quantified using the maximum amplitude values obtained by the automatic inspection apparatus for detecting stains on a polarizing plate using color difference analysis according to the embodiment of the invention. Since the quantified degree of staining coincides with the degree of staining observed with the naked eye, the maximum amplitude values obtained by the automatic inspection method according to the embodiment of the invention may be used to determine the visibility of (striped) stains on polarizing plates.

As set forth above, the automatic inspection apparatus and method for detecting stains on a polarizing plate using color difference analysis according to embodiments of the present invention may monitor the degree of staining on polarizing plates in a production line in real time without inspectors' inspection of individual polarizing plates. Accordingly, quality control and production efficiency may be enhanced, and required production time may be reduced.

In the automatic inspection apparatus and method for detecting stains on a polarizing plate using color difference analysis according to embodiments of the present invention, a target polarizing plate is arranged to have a certain level of brightness when an image thereof is captured, an image suitable for stain analysis may be obtained. Further, data extracted from the captured image is processed to increase a contrast range, and accordingly, a blurred stain may be detected more precisely.

In the automatic inspection apparatus and method for detecting stains on a polarizing plate using color difference analysis according to embodiments of the present invention, the degree of staining on polarizing plates is quantified based on an objective standard, whereby product quality may be uniformly maintained.

While the present invention has been shown and described in connection with the embodiments, it will be apparent to those skilled in the art that modifications and variations can be made without departing from the spirit and scope of the invention as defined by the appended claims.

What is claimed is:

1. An automatic inspection apparatus for detecting stains on a polarizing plate using color difference analysis, the automatic inspection apparatus comprising:
    an inspection unit including at least one reference polarizing plate and a target polarizing plate or polarizing element mounted on the at least one reference polarizing plate;
    a light source unit disposed on one surface of the inspection unit and irradiating the inspection unit with light;

an imaging unit disposed on the other surface of the inspection unit, imaging the target polarizing plate or polarizing element, and transferring an image thereof; and an arithmetic operation unit performing color difference analysis for individual inspection regions of the image of the target polarizing plate or polarizing element transferred by the imaging unit and detecting a blurred stain.

2. The automatic inspection apparatus of claim 1, wherein the arithmetic operation unit quantifies a degree of the blurred stain as a numerical data value.

3. The automatic inspection apparatus of claim 1, wherein the target polarizing plate or polarizing element is mounted on the reference polarizing plate.

4. The automatic inspection apparatus of claim 1, wherein the reference polarizing plate comprises at least two reference polarizing plates, and
the target polarizing plate or polarizing element is disposed between the at least two reference polarizing plates.

5. The automatic inspection apparatus of claim 4, wherein the at least two reference polarizing plates have parallel absorption axes.

6. The automatic inspection apparatus of claim 1, wherein the inspection unit further includes a rotating unit rotating the target polarizing plate or polarizing element.

7. The automatic inspection apparatus of claim 4, wherein the inspection unit further includes:
a first rotating unit rotating the target polarizing plate or polarizing element; and
a second rotating unit rotating a reference polarizing plate, disposed in a direction toward the imaging unit, of the at least two reference polarizing plates.

8. The automatic inspection apparatus of claim 6, wherein the inspection unit further includes:
a measuring unit measuring a level of brightness of the inspection unit while the inspection unit is irradiated with light; and
a controlling unit controlling the rotating unit according to a brightness value transferred by the measuring unit to determine an angle of rotation of the target polarizing plate or polarizing element.

9. The automatic inspection apparatus of claim 7, wherein the inspection unit further includes:
a measuring unit measuring a level of brightness of the inspection unit while the inspection unit is irradiated with light; and
a controlling unit controlling the first rotating unit according to a brightness value transferred by the measuring unit to determine an angle of rotation of the target polarizing plate or polarizing element, and controlling the second rotating unit based on the image captured by the imaging unit to determine an angle of rotation of the reference polarizing plate disposed in the direction toward the imaging unit.

10. The automatic inspection apparatus of claim 1, wherein the inspection unit is arranged to have a level of brightness of 2.5 to 20 nits by allowing absorption axes of the target polarizing plate and the reference polarizing plate to be inclined to each other.

11. The automatic inspection apparatus of claim 1, wherein the arithmetic operation unit includes:
a data extracting unit extracting location data and RGB data from the image transferred by the imaging unit;
a data processing unit processing the RGB data extracted by the data extracting unit to increase a contrast range thereof;
an inspection region setting unit setting the inspection regions using the location data extracted by the data extracting unit; and
a color difference analyzing unit performing detection and quantification of the blurred stain by analyzing color differences in the RGB data processed by the data processing unit with regard to the inspection regions set by the inspection region setting unit.

12. The automatic inspection apparatus of claim 11, wherein the data processing unit includes:
a converting part converting the RGB data extracted by the data extracting unit into hue, saturation and intensity data;
a processing part processing the intensity data among the converted data from the converting part in a histogram equalization scheme; and
a reconverting part combining the intensity data processed in the processing part with the hue and saturation data and reconverting the combined data into RGB data.

13. The automatic inspection apparatus of claim 11, wherein the inspection region setting unit sets the inspection regions by evenly dividing the image transferred by the imaging unit into at least 10 inspection regions in a machine direction.

14. The automatic inspection apparatus of claim 13, wherein the color difference analyzing unit includes:
a color difference calculating part calculating color differences in the individual inspection regions, analyzing the calculated color differences, and calculating a maximum color difference amplitude value; and
a detecting part quantifying the blurred stain using the maximum color difference amplitude value calculated in the color difference operating part.

15. The automatic inspection apparatus of claim 1, further comprising a display unit displaying results calculated in the arithmetic operation unit.

16. An automatic inspection method of detecting stains on a polarizing plate using color difference analysis, the automatic inspection method comprising:
mounting a target polarizing plate or polarizing element on at least one reference polarizing plate;
irradiating the target polarizing plate or polarizing element with light;
imaging the target polarizing plate or polarizing element; and
calculating color differences between individual pixels using data extracted from an image captured through the imaging of the target polarizing plate or polarizing element.

17. The automatic inspection method of claim 16, wherein the calculating of the color differences includes quantifying a degree of staining using calculated color difference data.

18. The automatic inspection method of claim 16, further comprising rotating the target polarizing plate or polarizing element to allow absorption axes of the target polarizing plate or polarizing element and the reference polarizing plate to be inclined to each other, between the irradiating and imaging of the target polarizing plate or polarizing element.

19. The automatic inspection method of claim 16, wherein the calculating of the color differences includes:
extracting data of the individual pixels from the image captured through the imaging of the target polarizing plate or polarizing element;
setting inspection regions by detecting locations of the individual pixels based on the extracted data;

calculating color differences of the individual pixels by detecting color coordinates of the individual pixels based on the extracted data within the inspection regions;

averaging the calculated color difference data of the individual pixels in a machine direction;

calculating a maximum color difference amplitude value by analyzing the averaged data in a transverse direction;

quantifying a degree of staining by comparing the maximum color difference amplitude value with a predetermined numerical data value indicating the degree of staining.

20. The automatic inspection method of claim 19, wherein the extracted data of the individual pixels includes RGB data and location data.

21. The automatic inspection method of claim 20, wherein the calculating of the color differences further includes performing data processing by processing the RGB data among the extracted data of the individual pixels to increase a contrast range thereof, between the extracting of the data of the individual pixels and the setting of the inspection regions.

22. The automatic inspection method of claim 21, wherein the data processing includes:
converting the RGB data among the extracted data of the individual pixels into hue, saturation and intensity data;
processing the intensity data extracted from the converted data in a histogram equalization scheme; and
reconverting the intensity data processed in the histogram equalization scheme and the hue and saturation data into RGB data.

23. The automatic inspection method of claim 16, further comprising displaying a degree of staining quantified during calculating of the color differences.

* * * * *